US012622795B1

(12) United States Patent
Sondreaal

(10) Patent No.: US 12,622,795 B1
(45) Date of Patent: May 12, 2026

(54) TAPERED SLEEVE

(71) Applicant: W. L. Gore & Associates, Inc., Newark, DE (US)

(72) Inventor: Matthew G. Sondreaal, Phoenix, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 18/419,760

(22) Filed: Jan. 23, 2024

Related U.S. Application Data

(63) Continuation of application No. 16/935,682, filed on Jul. 22, 2020, now Pat. No. 11,903,856, which is a continuation of application No. 15/704,505, filed on Sep. 14, 2017, now Pat. No. 10,751,205, which is a continuation of application No. 14/183,303, filed on Feb. 18, 2014, now Pat. No. 9,763,819.

(60) Provisional application No. 61/772,984, filed on Mar. 5, 2013.

(51) Int. Cl.
| | |
|---|---|
| *A61F 2/962* | (2013.01) |
| *A61F 2/958* | (2013.01) |
| *A61F 2/966* | (2013.01) |
| *A61F 2/07* | (2013.01) |

(52) U.S. Cl.
CPC ............... *A61F 2/962* (2013.01); *A61F 2/07* (2013.01); *A61F 2/958* (2013.01); *A61F 2002/9665* (2013.01)

(58) Field of Classification Search
CPC ................ A61F 2002/9511; A61F 2002/9665
See application file for complete search history.

(56) References Cited

U.S. PATENT DOCUMENTS

| | | | |
|---|---|---|---|
| 4,553,545 | A | 11/1985 | Maass et al. |
| 4,606,347 | A | 8/1986 | Fogarty et al. |
| 4,732,152 | A | 3/1988 | Wallsten et al. |
| 4,848,343 | A | 7/1989 | Wallsten et al. |
| 4,921,479 | A | 5/1990 | Grayzel |
| 5,064,435 | A | 11/1991 | Porter |
| 5,201,757 | A | 4/1993 | Heyn et al. |

(Continued)

FOREIGN PATENT DOCUMENTS

| | | |
|---|---|---|
| AU | 2019203691 B2 | 9/2020 |
| CN | 102341145 A | 2/2012 |

(Continued)

OTHER PUBLICATIONS

International Preliminary Report on Patentability received for PCT Patent Application No. PCT/US2014/020086, mailed on Jul. 16, 2015, 11 pages.

(Continued)

*Primary Examiner* — Sarah W Aleman

(57) ABSTRACT

The present disclosure describes methods of making a sleeve comprising a conical frustum having first and second end profiles and a lumen there through for covering and constraining an expandable device, and apparatuses, systems, and assemblies comprising an expandable device and a sleeve having a frustoconical shape when the expandable device is at least partially expanded. The present disclosure further describes methods for deploying an expandable device in a patient comprising releasing a releasable seam disposed on a sleeve and everting the sleeve while retracting it from the expandable device.

16 Claims, 4 Drawing Sheets

(56)          References Cited

U.S. PATENT DOCUMENTS

| | | | |
|---|---|---|---|
| 5,389,100 A | 2/1995 | Bacich et al. |
| 5,425,765 A | 6/1995 | Tiefenbrun et al. |
| 5,445,646 A | 8/1995 | Euteneuer et al. |
| 5,534,007 A | 7/1996 | St et al. |
| 5,571,135 A | 11/1996 | Fraser et al. |
| 5,647,857 A | 7/1997 | Anderson et al. |
| 5,662,703 A | 9/1997 | Yurek et al. |
| 5,755,769 A | 5/1998 | Richard et al. |
| 5,824,041 A | 10/1998 | Lenker et al. |
| 5,989,280 A | 11/1999 | Euteneuer et al. |
| 6,004,328 A | 12/1999 | Solar |
| 6,019,787 A | 2/2000 | Richard et al. |
| 6,039,721 A | 3/2000 | Johnson et al. |
| 6,042,605 A | 3/2000 | Martin et al. |
| 6,059,813 A | 5/2000 | Vrba et al. |
| 6,113,608 A | 9/2000 | Monroe et al. |
| 6,203,550 B1 | 3/2001 | Olson |
| 6,224,627 B1 | 5/2001 | Armstrong et al. |
| 6,238,410 B1 | 5/2001 | Vrba et al. |
| 6,254,628 B1 | 7/2001 | Wallace et al. |
| 6,315,792 B1 | 11/2001 | Armstrong et al. |
| 6,334,867 B1 | 1/2002 | Anson |
| 6,340,366 B2 | 1/2002 | Wijay |
| 6,350,278 B1 | 2/2002 | Lenker et al. |
| 6,352,553 B1 | 3/2002 | Van et al. |
| 6,352,561 B1 | 3/2002 | Leopold et al. |
| 6,364,904 B1 | 4/2002 | Smith |
| 6,383,171 B1 | 5/2002 | Gifford et al. |
| 6,398,758 B1 | 6/2002 | Jacobsen et al. |
| 6,524,335 B1 | 2/2003 | Hartley et al. |
| 6,533,806 B1 | 3/2003 | Sullivan et al. |
| 6,544,278 B1 | 4/2003 | Vrba et al. |
| 6,607,552 B1 | 8/2003 | Hanson |
| 6,645,242 B1 | 11/2003 | Quinn |
| 6,676,693 B1 | 1/2004 | Belding et al. |
| 6,733,521 B2 | 5/2004 | Chobotov et al. |
| 6,790,225 B1 | 9/2004 | Shannon et al. |
| 6,899,728 B1 | 5/2005 | Phillips et al. |
| 6,911,039 B2 | 6/2005 | Shiu et al. |
| 6,942,682 B2 | 9/2005 | Vrba et al. |
| 6,949,112 B1 | 9/2005 | Sridharan et al. |
| 6,974,471 B2 | 12/2005 | Van et al. |
| 7,081,132 B2 | 7/2006 | Cook et al. |
| 7,147,661 B2 | 12/2006 | Chobotov et al. |
| 7,198,636 B2 | 4/2007 | Cully et al. |
| 7,201,770 B2 | 4/2007 | Johnson et al. |
| 7,285,130 B2 | 10/2007 | Austin |
| 7,425,219 B2 | 9/2008 | Quadri |
| 7,632,296 B2 | 12/2009 | Malewicz |
| 7,645,298 B2 | 1/2010 | Hartley et al. |
| 7,655,034 B2 | 2/2010 | Mitchell et al. |
| 7,753,945 B2 | 7/2010 | Bruun et al. |
| 7,794,488 B2 | 9/2010 | Vrba et al. |
| 7,828,837 B2 | 11/2010 | Khoury |
| 7,837,724 B2 | 11/2010 | Keeble et al. |
| 7,938,851 B2 | 5/2011 | Olson et al. |
| 7,955,370 B2 | 6/2011 | Gunderson |
| 7,976,575 B2 | 7/2011 | Hartley |
| 8,016,872 B2 | 9/2011 | Parker |
| 8,147,538 B2 | 4/2012 | Brown et al. |
| 8,167,926 B2 | 5/2012 | Hartley et al. |
| 8,167,927 B2 | 5/2012 | Chobotov |
| 8,231,665 B2 | 7/2012 | Kim et al. |
| 8,241,346 B2 | 8/2012 | Chobotov |
| 8,257,431 B2 | 9/2012 | Henderson et al. |
| 8,262,671 B2 | 9/2012 | Osypka |
| 8,317,854 B1 | 11/2012 | Ryan et al. |
| 8,328,861 B2 | 12/2012 | Martin et al. |
| 8,361,135 B2 | 1/2013 | Dittman |
| 8,435,282 B2 | 5/2013 | Silverman |
| 8,480,725 B2 | 7/2013 | Rasmussen et al. |
| 8,540,760 B2 | 9/2013 | Paul et al. |
| 8,641,752 B1 | 2/2014 | Holm et al. |
| 8,764,816 B2 | 7/2014 | Koss et al. |
| 8,790,387 B2 | 7/2014 | Nguyen et al. |
| 8,801,774 B2 | 8/2014 | Silverman |
| 8,845,712 B2 | 9/2014 | Irwin et al. |
| 8,936,634 B2 | 1/2015 | Irwin et al. |
| 8,968,384 B2 | 3/2015 | Pearson et al. |
| 9,060,895 B2 | 6/2015 | Hartley et al. |
| 9,114,037 B2 | 8/2015 | Silverman |
| 9,132,025 B2 | 9/2015 | Aristizabal et al. |
| 9,186,487 B2 | 11/2015 | Dubrul et al. |
| 9,254,204 B2 | 2/2016 | Roeder et al. |
| 9,308,349 B2 | 4/2016 | Rezac et al. |
| 9,498,361 B2 | 11/2016 | Roeder et al. |
| 9,526,641 B2 | 12/2016 | Irwin et al. |
| 9,539,360 B2 | 1/2017 | Cully et al. |
| 9,585,743 B2 | 3/2017 | Cartledge et al. |
| 9,585,774 B2 | 3/2017 | Aristizabal et al. |
| 9,622,887 B2 | 4/2017 | Ducke et al. |
| 9,668,853 B2 | 6/2017 | Shin |
| 9,681,968 B2 | 6/2017 | Goetz et al. |
| 9,700,701 B2 | 7/2017 | Benjamin et al. |
| 9,763,819 B1 | 9/2017 | Sondreaal |
| 9,782,284 B2 | 10/2017 | Hartley et al. |
| 9,884,170 B2 | 2/2018 | Campbell et al. |
| 9,907,641 B2 | 3/2018 | Johnson |
| 9,937,070 B2 | 4/2018 | Skelton et al. |
| 10,213,329 B2 | 2/2019 | Cully et al. |
| 10,405,966 B2 | 9/2019 | Johnson |
| 10,966,850 B2 | 4/2021 | Irwin et al. |
| 11,229,539 B2 | 1/2022 | Cully et al. |
| 11,540,933 B2 | 1/2023 | Honeyfield et al. |
| 2001/0044595 A1 | 11/2001 | Reydel et al. |
| 2001/0056295 A1 | 12/2001 | Solem |
| 2002/0002397 A1 | 1/2002 | Martin et al. |
| 2002/0038141 A1 | 3/2002 | Yang et al. |
| 2002/0099431 A1 | 7/2002 | Armstrong et al. |
| 2002/0138129 A1 | 9/2002 | Armstrong et al. |
| 2003/0004561 A1 | 1/2003 | Bigus et al. |
| 2003/0105508 A1 | 6/2003 | Johnson et al. |
| 2003/0135258 A1 | 7/2003 | Andreas et al. |
| 2003/0149399 A1 | 8/2003 | Langan |
| 2003/0176910 A1 | 9/2003 | Vrba et al. |
| 2003/0199966 A1 | 10/2003 | Shiu et al. |
| 2003/0199967 A1 | 10/2003 | Hartley et al. |
| 2003/0212410 A1 | 11/2003 | Stenzel et al. |
| 2003/0233115 A1 | 12/2003 | Eversull et al. |
| 2004/0087886 A1 | 5/2004 | Gellman |
| 2004/0092977 A1 | 5/2004 | Vargas et al. |
| 2004/0143272 A1 | 7/2004 | Cully et al. |
| 2004/0143315 A1 | 7/2004 | Bruun et al. |
| 2004/0211433 A1 | 10/2004 | Albright |
| 2005/0049675 A1 | 3/2005 | Wallace |
| 2005/0059923 A1 | 3/2005 | Gamboa |
| 2005/0165352 A1 | 7/2005 | Henry et al. |
| 2005/0240254 A1 | 10/2005 | Austin |
| 2006/0015135 A1 | 1/2006 | Vrba et al. |
| 2006/0015171 A1 | 1/2006 | Armstrong |
| 2006/0030923 A1 | 2/2006 | Gunderson |
| 2006/0030924 A1 | 2/2006 | Van et al. |
| 2006/0041302 A1 | 2/2006 | Malewicz |
| 2006/0089627 A1 | 4/2006 | Burnett et al. |
| 2006/0122685 A1 | 6/2006 | Bonsignore et al. |
| 2006/0173422 A1 | 8/2006 | Reydel et al. |
| 2006/0184226 A1 | 8/2006 | Austin |
| 2006/0200221 A1 | 9/2006 | Malewicz |
| 2006/0206123 A1 | 9/2006 | Brenneman |
| 2006/0217796 A1 | 9/2006 | Dimatteo et al. |
| 2006/0282152 A1 | 12/2006 | Beyerlein et al. |
| 2007/0055358 A1 | 3/2007 | Krolik et al. |
| 2007/0060999 A1 | 3/2007 | Randall et al. |
| 2007/0093886 A1 | 4/2007 | Cully et al. |
| 2007/0142904 A1 | 6/2007 | Sorenson et al. |
| 2007/0191925 A1 | 8/2007 | Dorn |
| 2007/0208350 A1 | 9/2007 | Gunderson |
| 2007/0219612 A1 | 9/2007 | Andreas et al. |
| 2007/0244540 A1 | 10/2007 | Pryor |
| 2008/0140003 A1 | 6/2008 | Bei et al. |
| 2008/0140173 A1 | 6/2008 | Eskaros et al. |
| 2008/0167705 A1 | 7/2008 | Agnew |
| 2008/0255580 A1 | 10/2008 | Hoffman et al. |
| 2008/0281398 A1 | 11/2008 | Koss et al. |

(56)  References Cited

U.S. PATENT DOCUMENTS

| | | |
|---|---|---|
| 2008/0312662 A1 | 12/2008 | Hickingbotham |
| 2009/0018501 A1 | 1/2009 | Yribarren et al. |
| 2009/0099638 A1 | 4/2009 | Grewe |
| 2009/0125093 A1 | 5/2009 | Hansen |
| 2009/0143713 A1 | 6/2009 | Van et al. |
| 2009/0182411 A1 | 7/2009 | Irwin et al. |
| 2009/0192584 A1 | 7/2009 | Gerdts et al. |
| 2009/0234428 A1 | 9/2009 | Snow et al. |
| 2009/0254063 A1 | 10/2009 | Oepen et al. |
| 2009/0254170 A1 | 10/2009 | Hartley et al. |
| 2009/0270969 A1 | 10/2009 | Fargahi et al. |
| 2009/0299449 A1 | 12/2009 | Styrc |
| 2009/0326449 A1 | 12/2009 | Wang et al. |
| 2010/0004606 A1 | 1/2010 | Hansen et al. |
| 2010/0023106 A1 | 1/2010 | Meyer et al. |
| 2010/0036360 A1 | 2/2010 | Herbowy et al. |
| 2010/0036472 A1 | 2/2010 | Papp |
| 2010/0069852 A1 | 3/2010 | Kelley |
| 2010/0094398 A1 | 4/2010 | Malewicz |
| 2010/0100170 A1 | 4/2010 | Tan et al. |
| 2010/0168835 A1 | 7/2010 | Dorn |
| 2010/0234933 A1 | 9/2010 | Punga et al. |
| 2010/0331955 A1 | 12/2010 | Vrba et al. |
| 2011/0009943 A1 | 1/2011 | Paul et al. |
| 2011/0015716 A1 | 1/2011 | Silverman |
| 2011/0022154 A1 | 1/2011 | Hamer et al. |
| 2011/0034987 A1 | 2/2011 | Kennedy |
| 2011/0087318 A1 | 4/2011 | Daugherty et al. |
| 2011/0118765 A1 | 5/2011 | Aguirre |
| 2011/0118817 A1 | 5/2011 | Gunderson et al. |
| 2011/0137401 A1 | 6/2011 | Dorn et al. |
| 2011/0137402 A1 | 6/2011 | Dorn et al. |
| 2011/0166637 A1 | 7/2011 | Irwin et al. |
| 2011/0208292 A1 | 8/2011 | Von et al. |
| 2012/0016454 A1 | 1/2012 | Jantzen et al. |
| 2012/0059448 A1 | 3/2012 | Parker et al. |
| 2012/0078343 A1 | 3/2012 | Fish |
| 2012/0120287 A1 | 5/2012 | Funamoto et al. |
| 2012/0130472 A1 | 5/2012 | Shaw |
| 2012/0130473 A1 | 5/2012 | Norris et al. |
| 2012/0130474 A1 | 5/2012 | Buckley |
| 2012/0130475 A1* | 5/2012 | Shaw .................... A61F 2/07 |
| | | 623/1.35 |
| 2012/0143306 A1 | 6/2012 | Cully et al. |
| 2012/0165915 A1 | 6/2012 | Melsheimer et al. |
| 2012/0193018 A1 | 8/2012 | Banas et al. |
| 2012/0239134 A1 | 9/2012 | Dierking |
| 2012/0296406 A1 | 11/2012 | Minion |
| 2012/0296408 A1 | 11/2012 | Jones et al. |
| 2012/0296412 A1 | 11/2012 | Paul et al. |
| 2012/0323315 A1 | 12/2012 | Bruchman et al. |
| 2013/0006220 A1 | 1/2013 | Yribarren et al. |
| 2013/0035749 A1 | 2/2013 | Farag |
| 2013/0046371 A1 | 2/2013 | Greenberg et al. |
| 2013/0150949 A1 | 6/2013 | Silverman |
| 2013/0158524 A1 | 6/2013 | Fargahi |
| 2013/0172984 A1 | 7/2013 | Greenberg et al. |
| 2013/0178888 A1 | 7/2013 | Bliss et al. |
| 2013/0204343 A1 | 8/2013 | Shalev |
| 2013/0204345 A1 | 8/2013 | Cully et al. |
| 2013/0211493 A1* | 8/2013 | Wubbeling ............... A61F 2/95 |
| | | 623/1.11 |
| 2013/0238080 A1 | 9/2013 | Silverman |
| 2013/0245742 A1 | 9/2013 | Norris |
| 2013/0274851 A1 | 10/2013 | Kelly |
| 2013/0296877 A1 | 11/2013 | Irwin et al. |
| 2013/0340233 A1 | 12/2013 | Tollner et al. |
| 2014/0018610 A1 | 1/2014 | Von Pechmann et al. |
| 2014/0081376 A1 | 3/2014 | Burkart et al. |
| 2014/0130475 A1 | 5/2014 | Van et al. |
| 2014/0135895 A1* | 5/2014 | Andress .................. A61F 2/962 |
| | | 623/1.12 |
| 2014/0277347 A1 | 9/2014 | Daugherty et al. |

| | | |
|---|---|---|
| 2014/0358156 A1 | 12/2014 | Argentine |
| 2015/0134043 A1 | 5/2015 | Irwin et al. |
| 2015/0196383 A1 | 7/2015 | Johnson |
| 2015/0250630 A1 | 9/2015 | Irwin et al. |
| 2016/0045349 A1 | 2/2016 | Kilgrow et al. |
| 2016/0206418 A1 | 7/2016 | Johnsen et al. |
| 2017/0172724 A1 | 6/2017 | Cartledge et al. |
| 2017/0252161 A1 | 9/2017 | Tran et al. |
| 2017/0281382 A1 | 10/2017 | Lostetter et al. |
| 2019/0247210 A1 | 8/2019 | Cully et al. |
| 2020/0022800 A1 | 1/2020 | Johnson |
| 2020/0323670 A1 | 10/2020 | Honeyfield et al. |
| 2021/0186725 A1 | 6/2021 | Irwin et al. |
| 2022/0039940 A1 | 2/2022 | Johnson |
| 2022/0125610 A1 | 4/2022 | Cully et al. |
| 2023/0104877 A1 | 4/2023 | Honeyfield et al. |
| 2024/0033115 A1 | 2/2024 | Irwin et al. |
| 2024/0099828 A1 | 3/2024 | Johnson |
| 2024/0099865 A1 | 3/2024 | Majolagbe et al. |
| 2025/0169938 A1 | 5/2025 | Johnson |

FOREIGN PATENT DOCUMENTS

| | | |
|---|---|---|
| CN | 104023677 A | 9/2014 |
| CN | 106102596 A | 11/2016 |
| DE | 19531659 A1 | 3/1997 |
| EP | 1779809 A1 | 5/2007 |
| EP | 1441668 B1 | 1/2008 |
| EP | 2065015 A1 | 6/2009 |
| EP | 1915113 B1 | 3/2010 |
| EP | 2175813 A1 | 4/2010 |
| EP | 2352464 A1 | 8/2011 |
| EP | 1358903 B1 | 11/2011 |
| EP | 2491894 A1 | 8/2012 |
| EP | 2609895 A2 | 7/2013 |
| EP | 1474074 B1 | 4/2014 |
| EP | 2749251 B1 | 7/2016 |
| EP | 2956198 B1 | 11/2017 |
| EP | 3067014 B1 | 8/2019 |
| JP | 2000-279532 A | 10/2000 |
| JP | 2002-518086 A | 6/2002 |
| JP | 2002-537026 A | 11/2002 |
| JP | 2006-006648 A | 1/2006 |
| JP | 2007-534441 A | 11/2007 |
| JP | 2010-526583 A | 8/2010 |
| JP | 2011-509744 A | 3/2011 |
| JP | 2013-048778 A | 3/2013 |
| JP | 2017-511725 A | 4/2017 |
| JP | 2017-094144 A | 6/2017 |
| WO | 98/08456 A1 | 3/1998 |
| WO | 98/26731 A2 | 6/1998 |
| WO | 99/65420 A1 | 12/1999 |
| WO | 00/48645 A2 | 8/2000 |
| WO | 01/01886 A1 | 1/2001 |
| WO | 01/22903 A2 | 4/2001 |
| WO | 02/38084 A2 | 5/2002 |
| WO | 2005/107644 A1 | 11/2005 |
| WO | 2008/034793 A1 | 3/2008 |
| WO | 2008/137177 A2 | 11/2008 |
| WO | 2009/012061 A1 | 1/2009 |
| WO | 2009/091603 A1 | 7/2009 |
| WO | 2009/145901 A1 | 12/2009 |
| WO | 2010/063794 A1 | 6/2010 |
| WO | 2010/063795 A1 | 6/2010 |
| WO | 2010/120671 A1 | 10/2010 |
| WO | 2011/076408 A1 | 6/2011 |
| WO | 2012/054178 A1 | 4/2012 |
| WO | 2013/025470 A2 | 2/2013 |
| WO | 2014/107748 A2 | 7/2014 |
| WO | 2019/014634 A1 | 1/2019 |

OTHER PUBLICATIONS

International Search Report—PCT/2014/020086 dated Jun. 24, 2014.

* cited by examiner

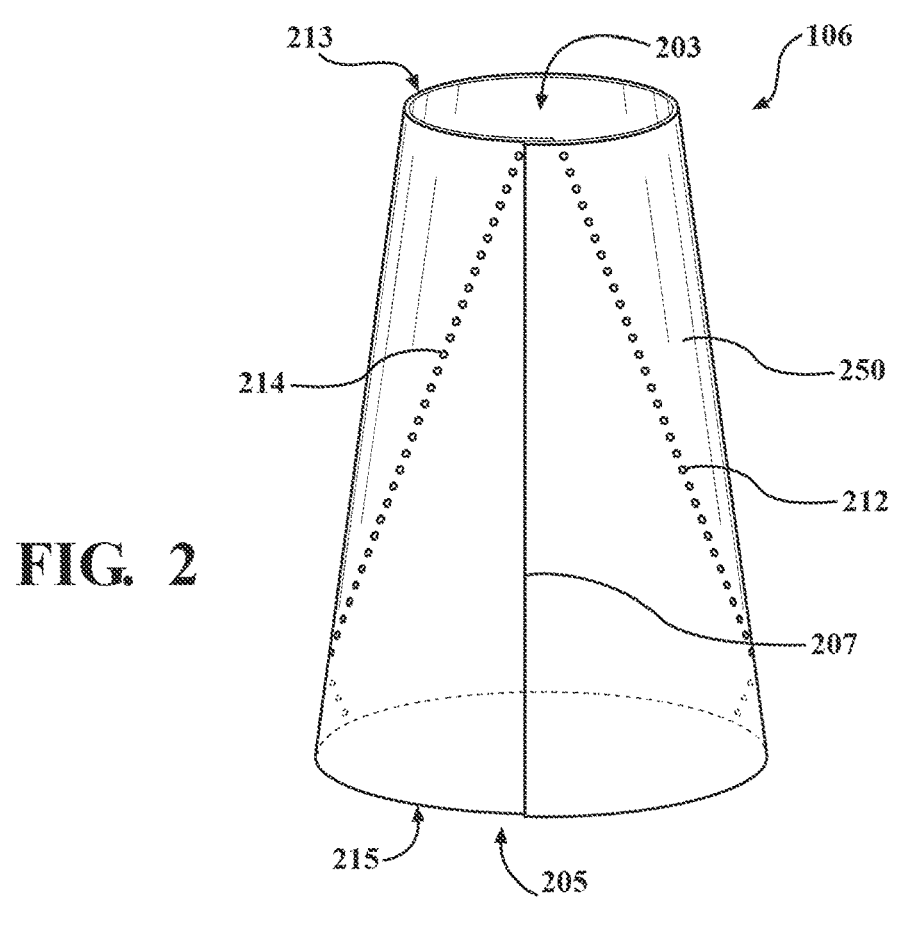
FIG. 2
FIG. 3
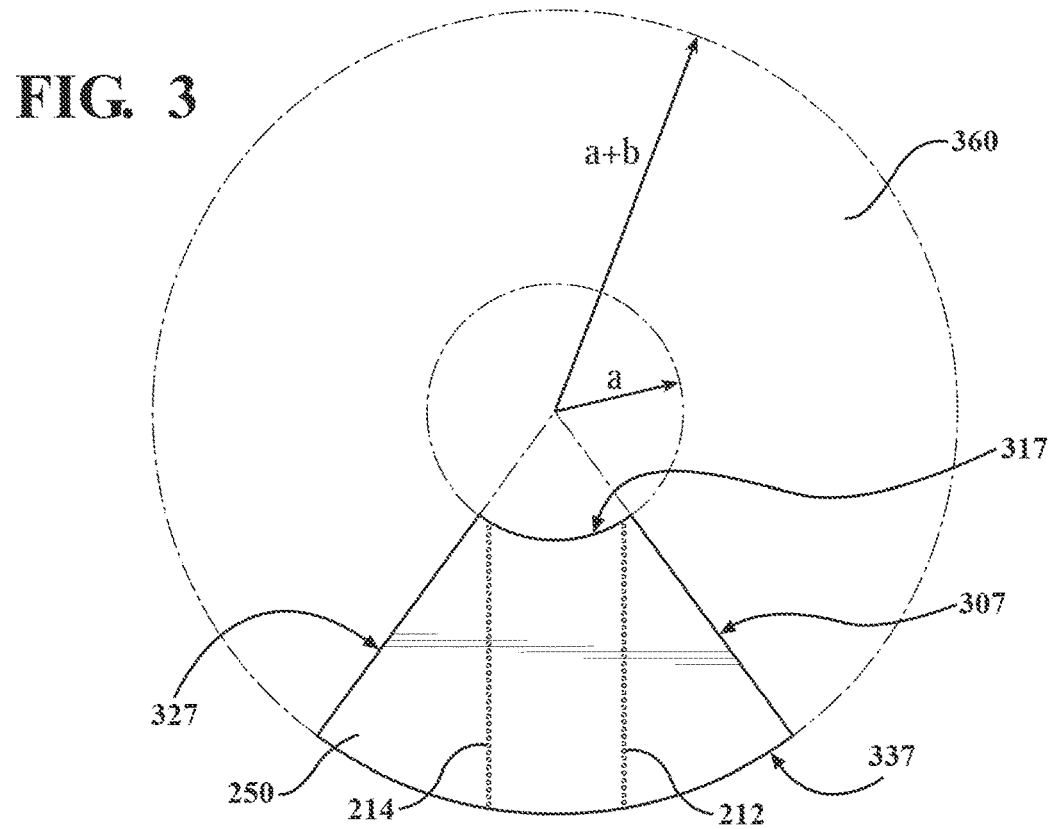

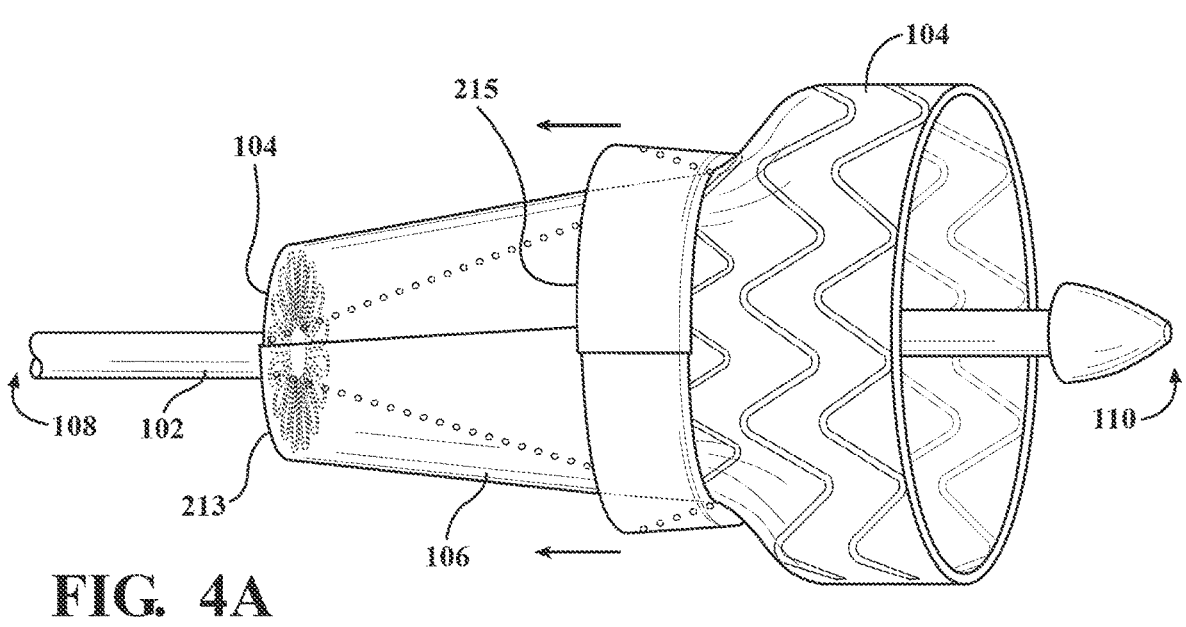
FIG. 4A
FIG. 4B
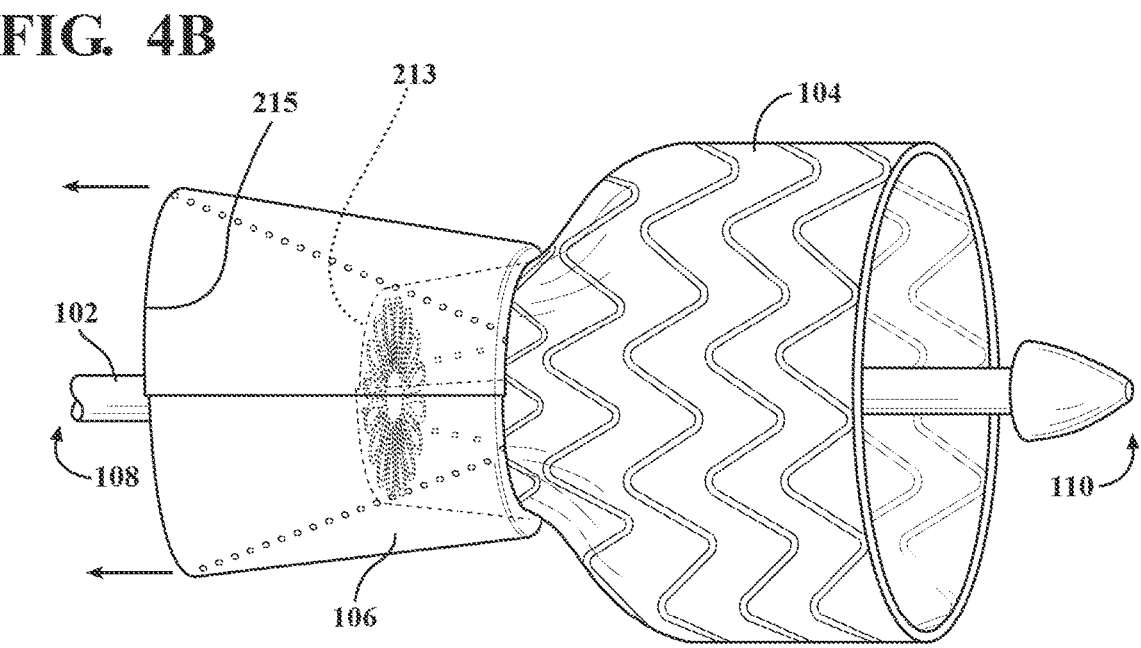

TAPERED SLEEVE

CROSS-REFERENCE TO RELATED APPLICATION

This application is a continuation of U.S. application Ser. No. 16/935,682, filed Jul. 22, 2020, which is a continuation of U.S. application Ser. No. 15/704,505, filed Sep. 14, 2017, now U.S. Pat. No. 10,751,205, issued Aug. 25, 2020, which is a continuation of U.S. application Ser. No. 14/183,303, filed Feb. 18, 2014, now U.S. Pat. No. 9,763,819, issued Sep. 19, 2017, which claims priority to U.S. Provisional Application No. 61/772,984, filed Mar. 5, 2013, all of which are herein incorporated by reference in their entireties.

FIELD

The present disclosure relates generally to the remote orientation and deployment of implantable medical devices and, more particularly, to implantable expandable devices surrounded by constraining sleeves.

BACKGROUND

Medical devices are frequently used to treat the anatomy of patients. Such devices can be permanently or semi-permanently implanted in the anatomy to provide treatment to the patient. Frequently, these devices, including stents, grafts, stent-grafts, filters, valves, occluders, markers, mapping devices, therapeutic agent delivery devices, prostheses, pumps, bandages, and other endoluminal and implantable devices, are inserted into the body at an insertion point and delivered to a treatment site using a catheter. Common types of expandable devices include stents and stent-grafts.

Expandable devices such as stents or stent-grafts are used in a variety of places in the human body to repair aneurysms and to support various anatomical lumens, such as blood vessels, respiratory ducts, gastrointestinal ducts, and the like. Expandable devices can have a reduced diameter when in a collapsed configuration, and can be designed to spontaneously dilate (i.e., elastically recover), or be balloon-expanded, from their collapse configuration, through one or more intermediate configurations, up to a maximum functional configuration. Expandable devices can be constrained in the collapsed configuration with a sleeve to facilitate transport to the treatment site.

The endoluminal delivery and deployment of expandable devices pose potential issues. First, the expandable device itself must be radially compacted to a suitable delivery configuration to allow insertion into the vasculature, constrained and mounted onto a delivery device such as a catheter. Subsequently, the constraint must be removed in order to allow the expandable device to expand or be expanded to its functional configuration and achieve the desired therapeutic outcome. A variety of ways of constraining and deploying an expandable device are known in the art. For example, an expandable device can be constrained by one or more sleeves with deployment comprising the removal of the one or more sleeves.

As such, there is an ongoing need to improve the endoluminal delivery and deployment of expandable devices such as stents and stent-grafts. New devices, assemblies and methods of deployment that can improve the use of sleeve-constrained expandable implants would be useful and desirable.

BRIEF DESCRIPTION OF THE DRAWINGS

The accompanying drawings are included to provide a further understanding of the disclosure. The drawings incorporated in and constituting a part of this specification illustrate embodiments of the disclosure, and together with the description, serve to explain the principles of the disclosure, wherein like numerals denote like elements and wherein:

FIG. 2 illustrates a perspective view of an embodiment of a sleeve in accordance with the present disclosure;

FIG. 3 illustrates an unwrapped sheet of material usable to form an embodiment of a sleeve in accordance with the present disclosure; and FIGS. 4A, 4B and 4C illustrate side views of an embodiment of an expandable device being deployed in accordance with the present disclosure.

DETAILED DESCRIPTION OF THE ILLUSTRATED EMBODIMENTS

Figure 1A:
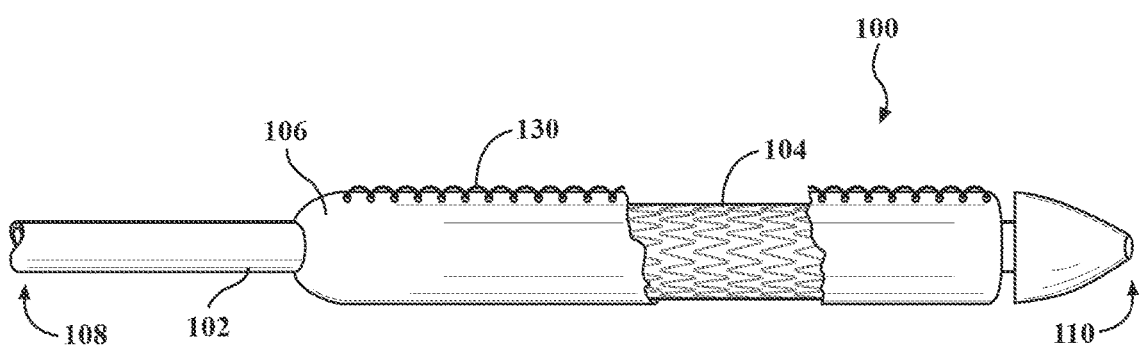
FIG. 1A illustrates a partial cutaway side view of an embodiment of an assembly comprising an expandable device constrained in a collapsed configuration in accordance with the present disclosure.

Persons skilled in the art will readily appreciate that various aspects of the present disclosure can be realized by any number of methods and systems configured to perform the intended functions. Stated differently, other methods and systems can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting.

With that said, and as will be described in more detail herein, various embodiments of the present disclosure generally comprise sleeves comprising a conical frustum usable for constraining expandable devices, assemblies comprising an expandable device and a sleeve having a frustoconical shape when the expandable device is in an intermediate configuration, and methods for deploying an expandable device in a patient comprising the eversion and retraction of a frustoconical-shaped sleeve from an expandable device.

As used herein, "proximal" indicates a position closer to the heart of the patient, or to a portion of a device that, when implanted, is closer to the heart of the patient than another portion of the device. "Distal" indicates a position farther from the heart of the patient, or to a portion of a device that, when implanted, is farther from the heart of the patient than another portion of the device. Implanted devices having tubular or rod-like shape comprise a distal end, a distal portion, a medial portion, a proximal portion, and a proximal end moving from the end farthest from the heart to the end closest to the heart.

With further regard to the terms proximal and distal, and because the present disclosure is not limited to peripheral and/or central approaches, this disclosure should not be narrowly construed with respect to these terms. Rather, the devices and method described herein can be altered and/or adjusted relative to the anatomy of a patient.

An "expandable device" can include, for example, any device suitable for delivery to the treatment site at a delivery diameter and capable of dilation from the diameter of the delivery profile, through a range of intermediary diameters, up to a maximal, pre-determined functional diameter. Such expandable devices can include endoluminal prostheses such as stents, grafts and stent-grafts.

As used herein, an "assembly" can include, for example, a combination of an expandable device, such as a stent or stent-graft, a delivery device, such as a catheter, and other related accessories, components, and devices.

As used herein, a "sleeve" can include any enclosure constraining an expandable device. In various embodiments, a sleeve can comprise a sheet of material wrapped around an expandable device in a collapsed, intermediate, or treatment configuration.

As used herein, the term "constrain" means: (i) to limit expansion, occurring either through self-expansion or assisted expansion, of the diameter of an expandable implant; or (ii) to cover or surround, but not otherwise restrain, an expandable implant such as for storage or biocompatibility reasons and/or to provide protection to the expandable implant and/or the vasculature.

As used herein, "deployment" refers to the actuation of a device at a treatment site, such as for example, the release and/or removal of a sleeve from a self-expanding device to allow the device to expand. The deployment process can be in stages, such as for example, a first stage comprising the release of a sleeve to a configuration suitable to constrain the expandable device only to an intermediate configuration, and a second stage comprising the removal of the sleeve altogether from the device.

As used herein, "conical frustum" means a portion of a hollow cone that lies between two parallel planes cutting it, or in other words, a truncated cone. As used herein, "frustoconical" means having the shape of a frustum of a cone.

As used herein, "eversion" means a process whereby a structure is turned inside-out. As used herein, "evert" means to turn something inside-out. An "everted" structure is a structure that has been everted, (i.e., turned inside-out).

Sleeves in accordance with the present disclosure can comprise a conical frustum that constrains an expandable device in an intermediate configuration. In various embodiments, a sleeve can be any other shape suitable for constraining an expandable device in a collapsed configuration. In various embodiments, a sleeve can change shape from a first shape that constrains an expandable device in a collapsed configuration, to a second shape that constrains the expandable device to an intermediate or fully expanded configuration. In various embodiments, a sleeve can be entirely removed from an expandable device by everting the sleeve while retracting it from the expandable device.

With reference now to FIGS. 1A, an assembly 100 in accordance with the present disclosure is illustrated in a partial cutaway side view. Assembly 100 comprises an expandable device 104 (viewable within the partial cutaway for discussion purposes), and at least one sleeve 106. As illustrated in FIG. 1A, the sleeve 106 circumferentially surrounds the expandable device 104, and constrains it in a collapsed configuration in which the diameter is less than the diameter of any intermediate configuration, which is less than the diameter of a fully expanded, treatment configuration. In various embodiments, the sleeve 106 can constrain an expandable device 104 to any intermediate diameter between the fully expanded diameter and the fully collapsed diameter. At least one coupling member 130 can coordinate with rows of openings disposed on the sleeve 106 to secure the sleeve 106 around the expandable device 104.

In various embodiments, the coupling member 130 can comprise a woven fiber or a monofilament fiber. Any type of string, cord, thread, fiber, or wire capable of constraining a sleeve around an expandable device is within the scope of the present disclosure. For example, the coupling member can comprise expanded polytetrafluoroethylene (ePTFE), ePTFE fiber such as (KORETEK®), sutures of polyethers such as polyethylene terephthalate (DACRON® or MYLAR®) or polyacrylamides such as KEVLAR®. The coupling member 130 may comprise a metal wire made from nitinol, stainless steel, or gold.

In various embodiments, the assembly 100 can include a catheter 102 having a distal end 108 and a proximal end 110. The expandable device 104 can be constrained in a collapsed configuration by sleeve 106 and mounted near the proximal end 110 of the catheter 102. The assembly 100 also has proximal and distal ends that correspond to those of the catheter 102.

In various embodiments, expandable device 104 comprises a stent-graft. Stent-grafts are designed to expand from a collapsed delivery diameter, through a range of intermediary diameters, up to a maximum, often pre-determined functional diameter, and generally comprise one or more stents and one or more graft members disposed over and/or under the stent.

In various embodiments, the expandable device 104 can comprise a stent. A stent can include, for example, a plurality of stent rings, cut tubes, wound wires (or ribbons) or flat patterned sheets rolled into a tubular form. Stent rings can be operatively coupled to one another with a wire. Stent components can be formed from metallic, polymeric or natural materials and can comprise conventional medical grade materials such as for example nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as iron alloys, stainless steels, cobalt-chromium alloys, nitinol, and the like; and biologically derived materials such as bovine arteries/veins, pericardium and collagen. Stent components can also comprise bioresorbable organic materials such as poly(amino acids), poly(anhydrides), poly(caprolactones), poly(lactic/glycolic acid) polymers, poly(hydroxybutyrates) and poly(orthoesters).

In various embodiments, expandable device 104 can be self-expanding. Such devices dilate from a radially collapsed configuration to a radially expanded configuration when unconstrained.

In various embodiments, expandable device 104 can be balloon-expandable with the assistance of a secondary device such as, for example, a balloon catheter or spring mechanism.

In various embodiments, the expandable device 104 can further comprise at least one graft member. The graft member can comprise, for example, expanded polytetrafluoroethylene (ePTFE), polyester, polyurethane, fluoropolymers, such as perfluoroelastomers and the like, polytetrafluoroethylene, silicones, urethanes, ultra high molecular weight polyethylene, aramid fibers, and combinations thereof. Other embodiments for graft material can include high strength polymer fibers such as ultra-high molecular weight polyethylene fibers (e.g., Spectra®, Dyneema Purity®, etc.) or aramid fibers (e.g., Technora®, etc.).

Figure 1B:
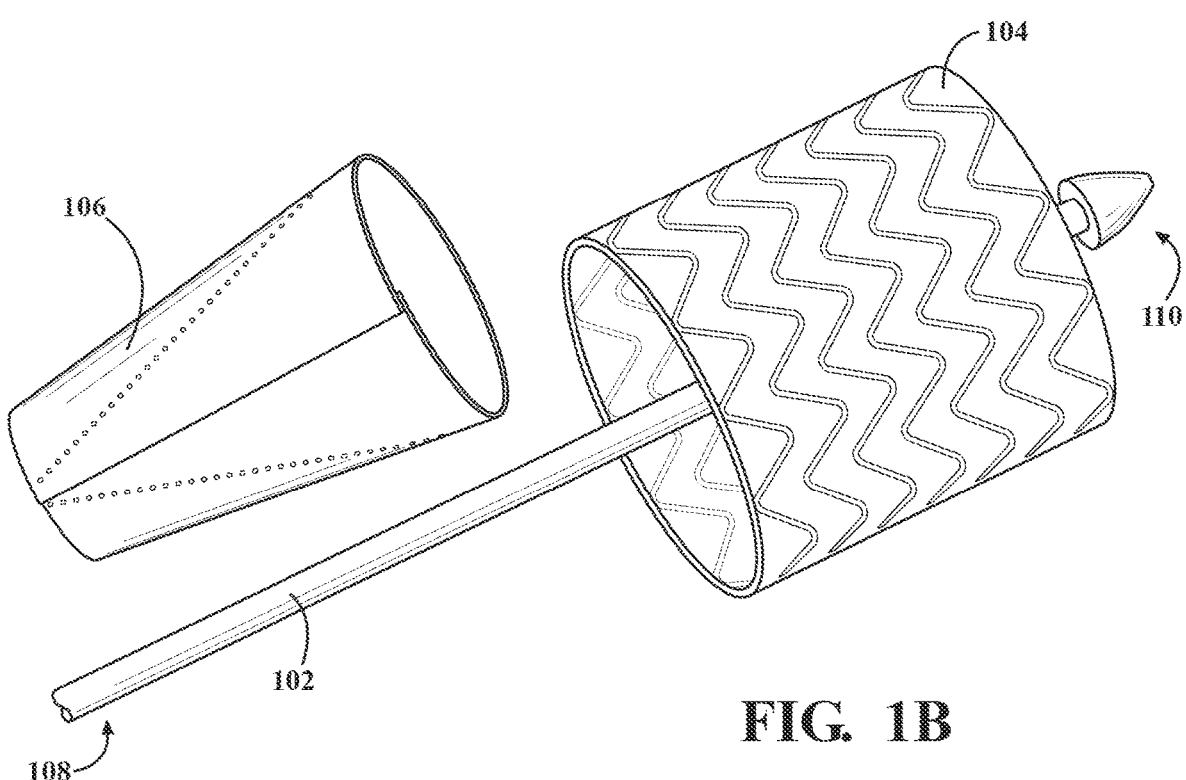
FIG. 1B illustrates side views of embodiments of an expanded device and a sleeve in accordance with the present disclosure.

As illustrated in FIG. 1B, expandable device 104, unconstrained by sleeve 106, can comprise a radially expanded configuration suitable for implant in the treatment area of a patient's vasculature. In the expanded configuration, the diameter of expandable device 104 can be approximately the same as the vessel to be repaired, or slightly larger than the vessel to be treated to provide a traction fit within the vessel. Prior to expansion of the expandable device 104 to the expanded configuration engaged with the vasculature, sleeve 106 may have constrained the expandable device 104 in an intermediate configuration. In various embodiments, the sleeve 106 can comprise a first end profile, a second end profile and a lumen extending between the end profiles, wherein the first end profile and second end profile are different. In various embodiments, the end profiles can be planar, and parallel. In some embodiments, planar end profiles need not be parallel. In various embodiments, the sleeve 106 can be frustoconical, with opposing end portions having planar circular perimeters parallel to each other. In various embodiments, either or both circular end portions can be non-planar.

Referring now to FIG. 2, sleeve 106 comprises a conical frustum having a first end profile 203 with first end profile perimeter 213, and a second end profile 205 with second end profile perimeter 215. In various embodiments, each of first end profile perimeter 213 and second end profile perimeter 215 are substantially circular, though they may have non-circular shapes in other embodiments. In various embodiments, first end profile 203 and second end profile 205 can be substantially planar and parallel to each other. In various embodiments, the difference in size between the first end profile 203 and the second end profile 205 can be about twice the wall thickness of the sleeve 106, or greater, as discussed below. In some embodiments, the difference in size need only be the difference required for the sleeve 106 to be everted.

Sleeve 106 further comprises a first seam 207 disposed between first end profile 203 and second end profile 205, though in other embodiments, sleeve 106 can be formed without such a seam. For example, sleeve 106 can be made by wrapping tape around a frustoconical mandrel and thermally bonding the windings into a sleeve, optionally leaving an end of the tape extending from the sleeve for attachment to one or more pull members (discussed below). In various other embodiments, sleeve 106 can be made by an extrusion process, or by stretching a cylindrical sleeve over a frustoconical mandrel into a tapered, frustoconical shape. Sleeve 106 can be formed from a sheet of material 250 wrapped into a frustoconical shape and joined along first seam 207. In various embodiments, first seam 207 can be perpendicular to both first end profile 203 and second end profile 205. By wrapping a sheet of material, sleeve 106 includes a lumen that extends through the conical frustum and connects the first end profile 203 and the second end profile 205. In various embodiments, first seam 207 can be releasable (i.e., it can be opened) or permanent.

In various embodiments, a sheet of material 250 of any particular thickness can be wrapped to form a frustoconical sleeve 106, wherein the difference in the diameter of second end profile 205 and the diameter of the first end profile 203 is equal to, or greater than, twice the thickness of the sheet of material 250.

In some embodiments, sleeve 106 further comprises a first row of openings 212 and a second row of openings 214 that can be coupled together into a releasable second seam with a coupling member (e.g., coupling member 130 in FIG. 1A) to reduce the overall size of sleeve 106, possibly change its shape, and constrain an expandable device within sleeve 106 to a collapsed delivery configuration.

In various embodiments, sleeve 106 can comprise materials similar to those used to form graft members. A sleeve can be made of any suitable material, including for example, a fluoropolymer such as ePTFE. Alternatively, or in combination with a fluoropolymer, the sleeve can be formed of biocompatible materials, such as polymers, which can include fillers such as metals, carbon fibers, Dacron, glass fibers or ceramics. Such polymers can include olefin polymers, polyethylene, polypropylene, polyvinyl chloride, polytetrafluoroethylene which is not expanded, fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, and combinations thereof. Also, polyesters, including polyethylene terephthalates, polypropylenes, polyethylenes, polyurethanes, polyolefins, polyvinyls, polymethylacetates, polyamides, naphthalane dicarboxylene derivatives, and natural silk can be included in the sleeve.

Referring now to FIG. 3, an unwrapped sheet of material 250 for forming a sleeve, such as for example sleeve 106, is illustrated. In various embodiments, sheet of material 250 can comprise the minor portion of an annulus 360 having minor arc of radius a and major arc of radius (a+b). First straight end 307 and second straight end 327 can be brought together to form first seam 207 (FIG. 2). In this way, the sheet of material 250 can be wrapped around an expandable device to constrain the expandable device in an intermediate configuration. In this way, the first seam 207 (FIG. 2), formed by joining the two opposite straight ends of the minor portion of the annulus, can have length approximately equal to b.

With continued reference to FIG. 3, sheet of material 250 can further comprise a first row of openings 212 and a second row of openings 214. The rows of openings can be linear and parallel to each other. In various embodiments, the first row of openings 212 can begin at a point where first straight end 307 meets the minor arced edge 317. Similarly, the second row of openings 214 can begin at a point where second straight end 327 meets the minor arced edge 317. Both rows of openings can extend out to the major arced edge 337 of the annulus portion as illustrated. As discussed, first row of openings 212 and second row of openings 214 can be joined into a releasable second seam with a coupling member threaded or woven through the openings. A coupling member can be of sufficient length to form a remote pull line used for tensioning and deployment of an expandable device constrained by a sleeve. When an expandable device is at the treatment site of the patient, the coupling member can be disengaged from the sleeve from outside of the body of the patient, which allows the sleeve to open along the releasable seam and the expandable device to expand or be available for assisted expansion.

Figure 4C:
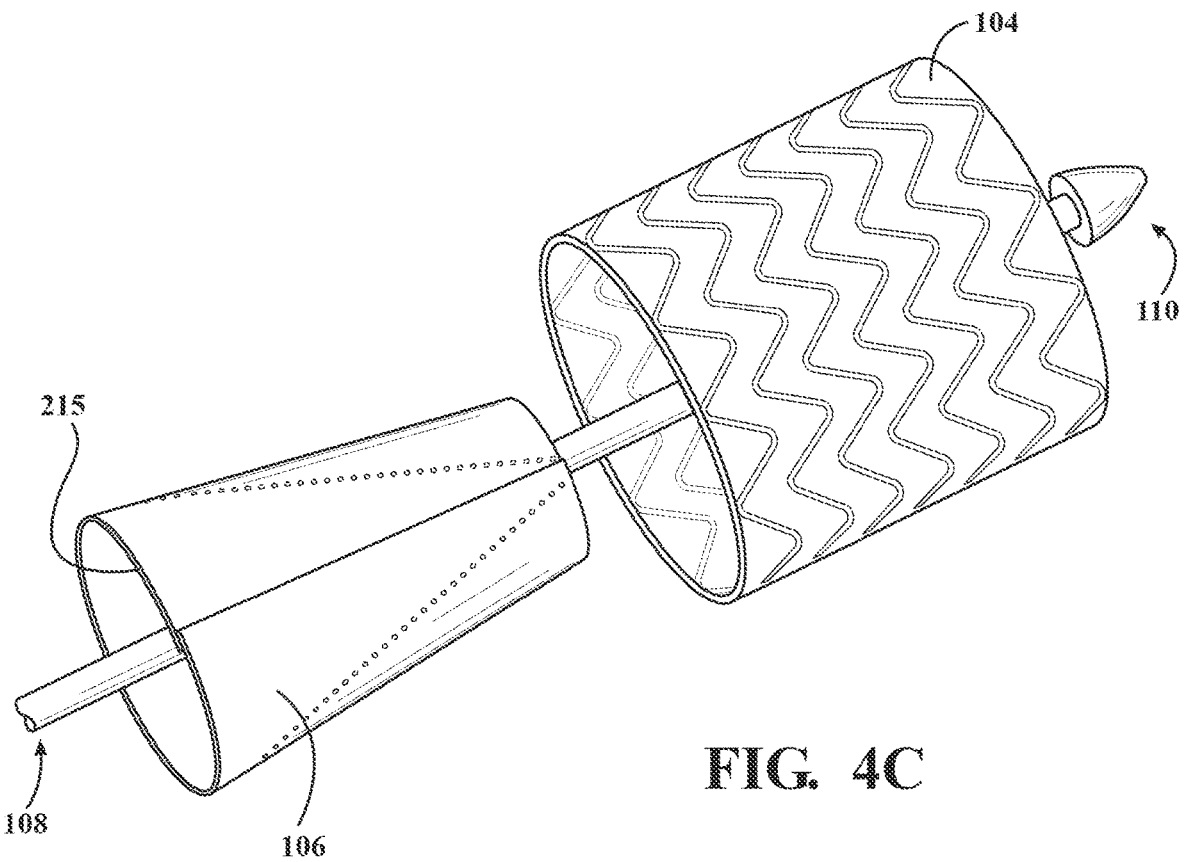

FIGS. 4A, 4B and 4C illustrate an embodiment of a method of deploying an expandable device in a patient in accordance with the present disclosure. In various embodiments, deployment of an expandable device can comprise at least two stages. For example, a first stage can comprise the opening of a releasable second seam on a sleeve, allowing an expandable device constrained therein to self-expand, or be available for expansion, from a collapsed delivery configuration to an intermediate configuration. In various embodiments, the tensioning and removal of a coupling member from the sleeve can operate to open the releasable second seam. The sleeve can comprise a conical frustum when the expandable device is in an intermediate configuration. For example, after tensioning and removal of a coupling member, the sleeve can comprise a conical frustum having a smaller first end profile at the distal end of the sleeve and a larger second end profile at the proximal end of the sleeve. In various embodiments, the sleeve, prior to the opening of the releasable second seam, can begin in a cylindrical shape, or in any other shape suitable to constrain the expandable device in a collapsed delivery configuration.

In various embodiments, the first stage of deployment can comprise the release of a primary sleeve that coaxially surrounds both an inner secondary sleeve and an expandable device. In this way, release of the primary sleeve allows the expandable device to self-expand, or to be available for expansion, to an intermediate configuration still constrained by a secondary sleeve comprising a conical frustum or other shape.

In various embodiments of a method for deploying an expandable device in a patient, a second stage can include retracting and removing a sleeve from the expandable device through eversion. For example, a frustoconical-shaped sleeve can be everted and removed from an expandable device by retracting the larger second end profile of the sleeve in a distal direction over the tapered body of the sleeve toward and over the smaller first end profile. In various embodiments, one or more remote pull lines can be tethered to the larger end profile of the sleeve to assist in a controlled and even retraction of the sleeve. For example, several pull lines can be tethered symmetrically around the second end profile. In various embodiments, the tethered pull line or pull lines can be formed as an integral portion of the larger end profile of the sleeve, such as through extension of a reinforcing fiber that circumscribes the larger end profile. These and other configurations for the larger end profile of the sleeve can help maintain strength and a low delivery profile for the sleeve.

By retraction of the larger end profile of the sleeve, the sleeve is everted as the larger second end profile is pulled over and past the smaller first end profile. By continued retraction, the sleeve is completely everted and removed from the expandable device, with the first smaller end profile of the sleeve departing from the distal end of the expandable device at the completion of the eversion process. As the sleeve is everted in this manner, the expandable device expands, or becomes available for expansion, from an intermediate configuration to a fully expanded treatment configuration. Optionally, once the sleeve is everted and removed, any unexpanded portions of the expandable device may be optionally expanded.

With reference now to FIG. 4A, sleeve 106 comprising a conical frustum is everted and retracted from expandable device 104 by pulling the larger second end profile perimeter 215 in the distal direction over the tapered body of sleeve 106 toward the smaller first end profile perimeter 213, as shown by the directional arrows. During the eversion, the larger second end profile perimeter 215 will circumferentially surround the tapered body of the sleeve as the larger second end profile perimeter 215 is retracted. With the expandable device in an intermediate configuration, rather than in a collapsed delivery configuration, the radial force from the expandable device 104 on the sleeve 106 has less impact on the eversion process. In this way, a sleeve comprising a conical frustum can be everted and pulled off an expandable device by retraction in the distal direction.

Referring now to FIG. 4B, further retraction of the second end profile perimeter 215 over and beyond the first end profile perimeter 213 in a distal direction continues to evert the sleeve 106 to ultimately free it from the expandable device 104.

Referring now to FIG. 4C, continued retraction of the second end profile perimeter 215 in a distal direction ultimately frees the sleeve 106 from the expandable device 104.

In this way, the sleeve 106 is turned inside-out when fully separated from the expandable device 104.

It will be apparent to those skilled in the art that various modifications and variations can be made in the present disclosure without departing from the spirit and scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. An endoprosthesis delivery system comprising:
an endoprosthesis defining a longitudinal length; and
an endoprosthesis constraining sleeve configured to constrain the endoprosthesis, the endoprosthesis constraining sleeve including:
a sleeve member configured to constrain the endoprosthesis in a delivery configuration and an intermediate deployment configuration and to release the endoprosthesis when in an everted configuration, the sleeve member configured to at least partially evert from the intermediate deployment configuration to the everted configuration, wherein the sleeve member surrounds the endoprosthesis along the longitudinal length when in the delivery configuration and the intermediate deployment configuration; and
a coupling member removably coupled to the sleeve member along at least a portion of a longitudinal length of the sleeve member, wherein the coupling member maintains the sleeve member in the delivery configuration when coupled to the sleeve member and wherein the sleeve member is free to expand to the intermediate deployment configuration when the coupling member is actuated,
wherein the sleeve member is without a seam in the intermediate deployment configuration.

2. The endoprosthesis delivery system of claim 1, wherein endoprosthesis is free to transition to a deployed configuration when the sleeve member is everted and not surrounding the endoprosthesis.

3. The endoprosthesis delivery system of claim 1, wherein coupling member is woven through the sleeve member to define a seam.

4. The endoprosthesis delivery system of claim 3, further comprising at least one remote pull line tether coupled to the second end and operable to evert the sleeve member when actuated.

5. The endoprosthesis delivery system of claim 1, wherein the sleeve member includes a first end, a body, and a second end, wherein the second end is configured to be actuated to everted over the body and the first end.

6. The endoprosthesis delivery system of claim 1, wherein the sleeve member is configured to transition from the delivery configuration to the intermediate deployment configuration when the coupling member is actuated and at least partially decoupled from the sleeve member.

7. The endoprosthesis delivery system of claim 1, wherein the sleeve member includes a tapered profile in the intermediate configuration such that the inner portion of the sleeve member has a first diameter at a first longitudinal position and a second diameter at a second longitudinal position, wherein the first diameter is greater than the second diameter.

8. The endoprosthesis delivery system of claim 7, wherein the tapered profile includes a frustoconical shape.

9. An endoprosthesis delivery system comprising an endoprosthesis; and an endoprosthesis constraining sleeve configured to constrain the endoprosthesis, the endoprosthesis constraining sleeve including:

a sleeve member defining a lumen extending longitudinally through the sleeve member, wherein the sleeve member is configured to at least partially evert;

a deployment line removably coupled to sleeve member along at least a portion of a longitudinal length of the sleeve member, wherein the deployment line is coupled to the sleeve member at a first circumferential position of the sleeve member and a second circumferential position of the sleeve member such that the first and second circumferential positions are adjacent each other when the deployment line is coupled to the sleeve member and the first and second circumferential positions are spaced from each other when the deployment line is removed; and a remote pull line extending from the sleeve member and configured to evert the sleeve member when actuated, wherein the sleeve member includes a first seam and a second seam, wherein the first seam is permanent and the the second seam is releasable via the deployment line.

10. The endoprosthesis delivery system of claim 9, wherein the sleeve member includes a delivery configuration, an intermediate deployment configuration, and a full deployment configuration.

11. The endoprosthesis delivery system of claim 10, wherein the sleeve member is operable to transition from the delivery configuration to the intermediate deployment configuration when the deployment line is actuated and decoupled from the sleeve member.

12. The endoprosthesis delivery system of claim 11, wherein the sleeve member is operable to transition from the intermediate deployment configuration to the full deployment configuration when the remote pull line is actuated to evert the sleeve member.

13. The endoprosthesis delivery system of claim 10, wherein the sleeve member includes a tapered profile in the intermediate deployment configuration such that the sleeve member has a first diameter at a first longitudinal position and a second diameter at a second longitudinal position, wherein the first diameter is greater than the second diameter.

14. The endoprosthesis delivery system of claim 13, wherein the tapered profile includes a frustoconical shape.

15. The endoprosthesis delivery system of claim 9, wherein the deployment line is woven through the sleeve member to define the second seam is releasable via the deployment line.

16. An endoprosthesis delivery system comprising:

an endoprosthesis defining a longitudinal length; and an endoprosthesis constraining sleeve configured to constrain the endoprosthesis, the endoprosthesis constraining sleeve including:

a sleeve member configured to constrain the endoprosthesis in a delivery configuration and an intermediate deployment configuration and to release the endoprosthesis when in an everted configuration, the sleeve member configured to at least partially evert from the intermediate deployment configuration to the everted configuration, wherein the sleeve member surrounds the endoprosthesis along the longitudinal length when in the delivery configuration and the intermediate deployment configuration; and a coupling member removably coupled to the sleeve member along at least a portion of a longitudinal length of the sleeve member, wherein the coupling member maintains the sleeve member in the delivery configuration when coupled to the sleeve member and wherein the sleeve member is free to expand to the intermediate deployment configuration when the coupling member is actuated, wherein the sleeve member includes a first seam and a second seam, and wherein the first seam is permanent and the second seam is releasable via the coupling member.

* * * * *